(12) United States Patent
Weber et al.

(10) Patent No.: US 9,120,105 B2
(45) Date of Patent: Sep. 1, 2015

(54) ELECTRONIC DEVICE FOR PATHOGEN DETECTION

(71) Applicants: Monika Weber, New Haven, CT (US); Mark A. Reed, Monroe, CT (US)

(72) Inventors: Monika Weber, Wroclaw (PL); Siu Lung Lo, Mid-levels (HK); Hazael Fabrizio Montanaro Ochoa, Asuncion (PY); Christopher Daniel Yerino, New Haven, CT (US); Mark A. Reed, Monroe, CT (US)

(73) Assignee: Monika Weber, New Haven, CT (US)

( * ) Notice: Subject to any disclaimer, the term of this patent is extended or adjusted under 35 U.S.C. 154(b) by 137 days.

(21) Appl. No.: 13/664,967

(22) Filed: Oct. 31, 2012

(65) Prior Publication Data

US 2013/0105317 A1     May 2, 2013

Related U.S. Application Data

(60) Provisional application No. 61/553,413, filed on Oct. 31, 2011, provisional application No. 61/557,654, filed on Nov. 9, 2011.

(51) Int. Cl.
    *G01N 27/447*      (2006.01)
    *B03C 5/02*      (2006.01)
    (Continued)

(52) U.S. Cl.
    CPC ........... *B03C 5/024* (2013.01); *B01L 3/502753* (2013.01); *B03C 5/005* (2013.01);
    (Continued)

(58) Field of Classification Search
    CPC .............. G01N 27/447; G01N 27/221; G01N 27/4145; G01N 33/487; B82Y 15/00; C12M 1/34; B03C 5/00; B03C 5/02; B03C 2201/26; B01L 2400/0424; B01L 3/502; B01L 2400/0487; B01L 2300/0874
    USPC ................. 204/450–453, 600–603; 422/68.1, 422/82.01
    See application file for complete search history.

(56) References Cited

U.S. PATENT DOCUMENTS 5,622,588 A     4/1997    Weber
5,814,200 A     9/1998    Pethig et al.
(Continued)

OTHER PUBLICATIONS

Markx, G., Huang, Y., Zhou, X.F., Pethig, R., "Dielectrophoretic Characterization and Separation of Micro Organisms, Microbiology" 140, 585-591, (1994).
(Continued)

*Primary Examiner* — Jennifer Dieterle
(74) *Attorney, Agent, or Firm* — Robert Curcio; DeLio, Peterson & Curcio, LLC

(57) ABSTRACT

An apparatus and method for separating an analyte from a test sample, such as bacteria from blood components, based on their dielectric properties, localizing or condensing the analyte, flushing substantially all remaining waste products from the test sample, and detecting low concentrations of the analyte. Species movement is caused by a module array imparting opposing dielectrophoretic forces. The module array includes a plurality of microfluidic channels with connecting microfluidic waste channels for directing undesired material away from the analyte. An electric field is applied causing a positive dielectrophoretic force to the analyte to capture the analyte. The Clausius-Mossotti factor of the analyte is changed by flushing the analyte with a reference solution, which causes a negative dielectrophoretic force to facilitate release of the analyte. A field effect nanowire or nanoribbon sensor detects the analyte after capture.

11 Claims, 16 Drawing Sheets

(51) Int. Cl.
G01N 33/487 (2006.01)
B03C 5/00 (2006.01)
B01L 3/00 (2006.01)
G01N 27/414 (2006.01)

(52) U.S. Cl.
CPC ...... *G01N 33/487* (2013.01); *B01L 2300/0874* (2013.01); *B01L 2400/0406* (2013.01); *B01L 2400/0424* (2013.01); *B01L 2400/0487* (2013.01); *B03C 2201/26* (2013.01); *G01N 27/4145* (2013.01)

(56) References Cited

U.S. PATENT DOCUMENTS

| | | | |
|---|---|---|---|
| 6,071,394 | A | 6/2000 | Cheng et al. |
| 6,280,590 | B1 | 8/2001 | Cheng et al. |
| 6,576,459 | B2 | 6/2003 | Miles et al. |
| 6,875,329 | B2 | 4/2005 | Washizu et al. |
| 6,887,362 | B2 | 5/2005 | Huang et al. |
| 6,989,086 | B2 | 1/2006 | Cheng et al. |
| 7,081,192 | B1 | 7/2006 | Wang et al. |
| 7,153,648 | B2 | 12/2006 | Jing et al. |
| 7,169,282 | B2 | 1/2007 | Talary et al. |
| 7,198,702 | B1 | 4/2007 | Washizu et al. |
| 7,384,791 | B2 | 6/2008 | Tyvoll et al. |
| 7,390,387 | B2 | 6/2008 | Childers |
| 7,390,388 | B2 | 6/2008 | Childers |
| 7,534,334 | B1 | 5/2009 | Fiechtner |
| 7,615,762 | B2 | 11/2009 | Satyanarayana |
| 7,658,829 | B2 | 2/2010 | Kanagasabapathi et al. |
| 7,666,289 | B2 | 2/2010 | Simmons |
| 7,686,934 | B2 | 3/2010 | Hodko et al. |
| 7,744,738 | B1 | 6/2010 | Gagnon et al. |
| 8,029,657 | B1* | 10/2011 | Wu .............. 204/547 |
| 2004/0011651 | A1* | 1/2004 | Becker et al. ......... 204/547 |
| 2004/0077074 | A1* | 4/2004 | Ackley et al. ....... 435/287.2 |
| 2004/0109793 | A1 | 6/2004 | McNeely |
| 2004/0226819 | A1 | 11/2004 | Talary et al. |
| 2007/0125650 | A1* | 6/2007 | Scurati et al. ......... 204/547 |
| 2008/0221806 | A1* | 9/2008 | Bryant et al. ............ 702/22 |
| 2009/0294291 | A1 | 12/2009 | Voldman et al. |
| 2009/0304644 | A1* | 12/2009 | Hedrick et al. ......... 424/93.7 |
| 2011/0147917 | A1 | 6/2011 | England |

OTHER PUBLICATIONS

Vahey, M.D., Voldman, J., "High-Throughput Cell and Particle Characterization Using Isodielectric Separation", Anal. Chemistry, 2009, 81 (7), 2446-2455.

Kuczenski, R., Chang, H., Revzin, A., "Dielectrophoretic Microfluidic Device for the Continuous Sorting of *Escherichia coli* From Blood Cells", Biomicrofluidics, 5, 032005, (2011).

Stern, E., Steenblock, E.R., Reed, M.A., Fahmy, T.M., "Label-Free Electronic Detection of the Antigen-Specific T-Cell Immune Response", Nano Lett. 8, 3310 (2008).

Vacic, A, Criscione, J.M., Stern, E., Rajan, N.K., Fahmy, T.M., Reed, M.A., "Multiplexed Soi Biofets", Biosens. Bioelectron., 28, 239-242 (2011).

Beving, H., Eriksson, L.E.G., Davey, C.L., Kell, D.B., "Dielectric Properties of Human Blood And Erythrocytes At Radio Frequencies (0.2-10 Mhz); Dependence On Cell Volume Fraction and Medium Composition", Eur Biophys J., 23, 207-215 (1994).

Yang, J., Huang, Y., Wang, X., Becker, F., Gascoyne, P., "Differential Analysis of Human Leukocytes by Dielectrophoretic Field-Flow-Fractionation", Biophysical Journal, 78, 2680-2689, (2000).

Yang, J., Huang, Y., Wang, X., Becker, F., Gascoyne, P., "Dielectric Properties of Human Leukocyte Subpopulations Determined by Electrorotation as a Cell Separation Criterion", Biophysical Journal, 76, 3307-3314, (1999).

Pethig, R., Review Article—Dielectrophoresis: Status of the Theory, Technology, and Applications, Biomicrofluidics, 022811, (2010).

Pohl, H., Hawk, I., "Separation Of Living And Dead Cells By Dielectrophoresis", Science, 152, 3722 (1968).

Huang, Y., Holzel, R., Pethig, R., Wang, X, "Differences In The Ac Electrodynamics Of Viable And Non-Viable Yeast Cells Determined Through Combined Dielectrophoresis and Electrorotation Studies", Phys. Med. Bid., 37,7, (1992).

Chang, S., Cho, Y., "A Continuous Size-Dependent Particle Separator Using a Negative Dielectrophoretic Virtual Pillar Array", Lab Chip, 8, 1930-1936, (2008).

Choi, Jae-Woo, Rosset, S., Niklaus, M., Adleman, J.R., Shea, H., Psaltis, D., "3-Dimensional Electrode Patterning Within A Microfluidic Channel Using Metal ION Implantation", Lab On A Chip, vol. 10, Issue: 6, pp. 783-788, (2010).

Stern, E., Vacic, A., Rajan, N.K., Criscione, J.M., Park, J., Ilic, B.J., Mooney, D.J., Reed, M.A., Fahmy, T.M., "Label-free biomarker detection from whole blood", Nature Nanotechnology 5, 138-142 (2010).

Sher, L., "Dielectrophoresis in Lossy Dielectric Media", Nature 220, 695-696, 1968.

Voldman, J., "Electrical Forces for Microscale Cell Manipulation", Annual Review of Biomedical Engineering, vol. 8: 425-454, (2006).

Cheng, I.F.; Chang, H.C.; Hou, D.; Chang, H.C.; "An Integrated Dielectrophoretic Chip For Continuous Bioparticle Filtering, Focusing, Sorting, Trapping, And Detecting, Biomicrofluidics" 1, 021503 (2007).

Unni, H.N., Hartono, D., Yue, L., Yung, L., Ng, M., Lee, H. P., Khoo, B.C., Lim, K.M, "Characterization And Separation Of Cryptosporidium And Giardia Cells Using On-Chip Dielectrophoresis", Biomicrofluidics 6, 012805 (2012).

Fritz, G. Jr., "Anomalous Diffusion Of Erythrocytes In The Presence of Polyvinylpyrrolidone", Biophys. J. vol. 46 Aug. 1984 219-228, (1984).

Cho, S.K, Hyejin, M., Kim, C.J., "Creating, Transporting, Cutting, and Merging Liquid Droplets by Electrowetting-Based Actuation for Digital Microfluidic Circuits", J Mems, 12 70, (2003).

Surowiect, A., Stuchly, S., Izaguirre, C., "Dielectric Properties of Human B and T Lymphocytes At Frequencies From 20 Khz To 100 Mhz", Phys. Med. Biol., 31, 1 (1986).

Cociancich, S., Ghazi, A., Hetru, C., Hoffmann, J., Letelliers, L., "Insect Defensin, an Inducible Antibacterial Peptide, Forms Voltage-Dependent Channels in *Micrococcus luteus*" Journal of Biological Chemistry, vol. 268 Iss:26 p. 19239-19245, (1993).

Printen, J.A., Woodard, S.L., Herman, J.R., Roess D.A., Barisas, B.G., "Membrane Changes in Lipopolysaccharide-Stimulated Murine B-Lymphocytes Associated With Cell Activation", Biochimica Et Biophysica Acta, 1148 91-96, (1993).

Carstensen, E.L., "Passive Electrical Properties of Microorganisms", Biophysical Journal, vol. 7, (1967).

Shah, G.J., Veale, J.L., Korin, Y., Reed, E.F., Gritsch H.A., "Specific binding and magnetic concentration of CD8+ T-lymphocytes on electrowetting-on-dielectric platform", Biomicrofluidics 4, 044106 (2010).

Lee, J., Moon, H., Fowler, J., Schoellhammer, T., Kim, C.J., "Electrowetting and Electrowetting-On-Dielectric for Microscale Liquid Handling" Sensors and Actuators A. 95 259 (2002).

Pollack, M.G., Shenderov, A.D., Fair, R.B., "Electrowetting-Bsed Actuation of Droplets for Integrated Microfluidics" Lab Chip 2 96 (2002).

Pollack, M.B., Fair, R.B., Shenderov, A.D., "Electrowetting-Based Actuation of Liquid Droplets for Microfluidic Applications", Appl. Phys. Lett 11 1725 (2000).

Pohl, H.A.; Kaler, Karan; Pollock, Kent; "The Continuous Positive and Negative Dielectrophoresis of Microorganisms", Forum Press, Inc., 67-86 (1981).

* cited by examiner

TABLE I

| | real ε | imag ε | σ [S/m] | radius r[um] | serum at 10MHz α*1e-24 | real CM |
|---|---|---|---|---|---|---|
| Ecoli | 180 | 324 | 0.18 | 1.6 | -0.0044 | -0.2575 |
| Micrococcus | 300 | 540 | 0.3 | 1.7 | -0.0027 | -0.1308 |
| T lymphocyte | 100 | 540 | 0.3 | 3.3 | 0.0136 | 0.0906 |
| Monocytes | 127 | 1008 | 0.56 | 4.6 | 0.0161 | 0.0396 |
| B-lymphocyte | 154 | 1313 | 0.73 | 3.3 | 0.0201 | 0.1338 |
| Granulocyte | 151 | 1080 | 0.6 | 4.7 | 0.0278 | 0.0642 |
| RBC | 500 | 1709 | 0.95 | 3.5 | 0.0437 | 0.2445 |

FIG. 8

TABLE II

|  | PBS @ 10MHz | | serum @ 400MHz | |
|---|---|---|---|---|
|  | α*1e-24 | real CM | α*1e-24 | real CM |
| Ecoli | 0.0055 | 0.3005 | 0.0044 | 0.2681 |
| Micrococcus | 0.0106 | 0.4853 | 0.0043 | 0.2305 |

FIG. 10

ELECTRONIC DEVICE FOR PATHOGEN DETECTION

BACKGROUND OF THE INVENTION

1. Field of the Invention

The invention relates to an apparatus and method for pathogen detection. Specifically, the invention relates to the field of pathogen detection systems and diagnostic devices and their micro-component assembly. More specifically, the invention utilizes an apparatus that includes a dielectrophoretic separator, a dielectrophoretic condenser, a dielectrophoretic trap, microfluidic components, and field effect sensor, such as an ion sensitive sensor, nanowire sensor, or nanoribbon sensor configured as biosensors, to perform a pathogen detection process.

2. Description of Related Art

Bacterial infections cause thousands of diseases in humans and animals every year. Recent deadly outbreaks of *E. Coli*, *Salmonella*, and *Listeria* have highlighted the urgent need for more effective methods of detection, identification, and characterization of pathogens, and their origin and proliferation. Conventional detection methods have proven inadequate because they suffer from long incubation periods, high cost, and require highly trained personnel to operate. There remains a strong need for a reliable, time-efficient apparatus and method for specific detection of bacteria in low concentration.

Conventional methods rely on bacterial culture growth, which require highly qualified personnel and time, both contributing to higher costs for the procedure. The most widely used method for bacterial detection, the standard plate count, takes from 24 to 48 hours due to the time needed for bacteria to grow detectable colonies, and requires a stocked microbiology lab. Although faster methods, such as PCR (Polymerase Chain Reaction) Plates or labeled detection and fluorescent imaging, can reduce the response time to one hour, these require complex sample preparation, highly trained personnel, high cost per test, and have limited portability.

The major challenge in automated sample preparation for detection from blood or other unprocessed liquids using microstructures is efficient separation of the analyte of interest (bacteria, cells, or particles) from large blood components. Red blood cells (RBC) and white blood cells (WBC) range between 6 μm-21 μm in size and constitute over 50% of the whole blood volume. RBC and WBC presence obstructs the detection of bacteria, cells, or particles. The present invention is a miniaturized device for rapid pathogen screening that overcomes these obstacles.

Dielectrophoresis ("DEP") is a separation method based on size and dielectric properties and has been described in literature as for example in Pohl et al, Science 1966, and Sher Nature 1968, Voldman, Annual Review Of Biomedical Engineering, 2006. The use of DEP to manipulate particles and cells has been previously described, as for example, in H. Pohl, I. Hawk, "Separation Of Living And Dead Cells By Dielectrophoresis," Science, 152, 3722 (1966); Y. Huang, R. Holzel, R. Pethig, X. Wang, "Differences In The Ac Electrodynamics Of Viable And Non-Viable Yeast Cells Determined Through Combined Dielectrophoresis And Electrorotation Studies," Phys. Med. Bid., 37, 7 (1992); S. Chang, Y. Cho, "A Continuous Size-Dependent Particle Separator Using A Negative Dielectrophoretic Virtual Pillar Array," Lab Chip, 8, 1930-1936 (2008); and J. Yang, Y. Huang, X. Wang, F. Becker, P. Gascoyne, "Differential Analysis Of Human Leukocytes By Dielectrophoretic Field-Flow-Fractionation," Biophysical Journal, 78, 2680-2689 (2000). However, effective methods for cell/pathogen separation on a micro-scale from fluids containing pollutants of comparable size are still unattainable.

High-frequency electric fields when applied to an electrically neutral object cause polarization. A high-frequency non-uniform electric field gives rise to a dielectrophoretic force (DEP) $F_{DEP}$ which acts on the object.

A spherical object of a given electrical permittivity $\in_p$ placed in a medium of a different permittivity $\in_m$ in a spatially varying electric field $E(x,\omega)$ is subjected to a dielectrophoretic force, $F_{DEP}$. The dielectrophoretic force is given by:

$$F_{DEP} = 2\pi \in_m r^3 \text{Re}\{CM(\omega)\} \cdot \nabla E^2$$

where $$CM(\omega) = (\tilde{\in}_p - \tilde{\in}_m)/(\tilde{\in}_p + 2\tilde{\in}_m)$$

$$\tilde{\in} = \in + \sigma/i\omega;$$

$CM(\omega)$ is the Clausius-Mossotti factor;
$\text{Re}\{CM(\omega)\}$ is the real part of the $CM(\omega)$, which can be a complex number;
$\in_p$ is the particle permittivity;
$\in_m$ is the permittivity of the liquid medium;
$r$ is the particle radius;
$\tilde{\in}$ is the complex permittivity (complex dielectric function);
$\sigma$ is the conductivity;
$i$ is the imaginary unit;
$\omega$ is the angular frequency; and
$\nabla E$ is the gradient of the electric field Depending on the respective permeability ($\tilde{\in}$) and conductivity ($\sigma$) of the object and the medium, the force can be attractive (positive dielectrophoresis (pDEP)), or repulsive (negative dielectrophoresis (nDEP)). If $\text{Re}\{CM(\omega)\}$ is positive, then the particle experiences a positive dielectrophoretic force, and if $\text{Re}\{CM(\omega)\}$ is negative, then the particle experiences a negative dielectrophoretic force. Different species have different dielectric properties. The dielectric functions $\in_m$, $\in_p$ depend on the frequency of the external electric field. The permittivity of the medium affects the $CM(\omega)$ factor and the value of $\text{Re}\{CM(\omega)\}$. Importantly, if the signs of $\text{Re}\{CM(\omega)\}$ for different species are opposite then the species are subject to forces acting in opposite directions and separation occurs.

There is a cross-over frequency, $\omega_{co}$, that occurs when the $\text{Re}\{CM(\omega)\}$ goes to zero. Critical to separation is that $\omega_{co}$ is uniquely different for different cells and bacteria. Separation procedures for stained cells have been described in U.S. Pat. No. 7,153,648 entitled "Dielectrophoretic Separation Of Stained Cells," where appropriate frequency and amplitude are applied via a function generator, and red blood cells are attracted to electrodes by positive dielectrophoresis force, while stained white blood cells are repelled to the area with weakest electric field by negative dielectrophoresis force. The differential behavior and separation of *E. Coli* cells from human blood cells on electrodes under applied electric field has been described in U.S. Pat. No. 6,989,086 entitled "Channel-less separation of bioparticles on an Electronic Chip by Dielectrophoresis."

The dielectrophoretic force is affected both by the geometry of the electrodes (gradient of the electric field), the $\text{Re}\{CM(\omega)\}$ factor, and depends on the dielectric constant of the medium $\in_m$.

Using the aforementioned prior art techniques for dielectrophoresis, the separation of bacteria from blood may achieve, at best, an efficiency of approximately 30%.

SUMMARY OF THE INVENTION

Bearing in mind the problems and deficiencies of the prior art, it is therefore an object of the present invention to provide a filtration system for pathogen detection that utilizes a plurality of dielectrophoretic modules with distinctive functionality and geometry to obtain separation performance which cannot be obtained using the single module apparatus of the prior art.

It is another object of the present invention to provide a pathogen detection system that includes a capture/release mechanism for solution exchange without cell loss to enhance pathogen detection at low concentrations.

It is yet another object of the present invention to provide a method for separating a low concentration of bacteria (or other pathogens/particles) from a high volume of blood (or other fluids) which is based on the dielectric properties of the products. The species separation being enhanced and promoted by dielectrophoretic forces acting on the test sample in a plurality of microfluidic channels.

It is another aspect of the present invention to provide a filtration system for pathogen detection that can accommodate high and low throughput, capable of processing test sample volumes significantly greater than micro- or picoliters, yet capable of processing the minute test sample volumes as well.

It is another object of the present invention to provide pathogen detection in liquid media, especially for use with food and agricultural products to improve health standards at the consumer level.

It is another object of the present invention to provide time sensitive pathogen detection for point-of-care diagnostics.

Still other objects and advantages of the invention will in part be obvious and will in part be apparent from the specification.

The above and other objects, which will be apparent to those skilled in the art, are achieved in the present invention which is directed to an apparatus for pathogen detection comprising: a first chamber for storing a test sample including product to be analyzed and microscaled components to be separated from the product to be analyzed; a second chamber for storing a reference solution; a pump for pumping the test sample and the reference solution; a microfluidic separator separating the product to be analyzed from the microscaled components, the microfluidic separator including a plurality of microfluidic channels, each microfluidic channel including: electrodes for producing a dielectrophoretic force on the test sample when the test sample is pumped through each of the microfluidic channels to perform a dielectrophoresis-based separation; and channels for transporting the microscaled components away from the product to be analyzed; a third chamber for storing the microscaled components when separated from the product to be analyzed by the plurality of microfluidic channels; a condenser for capturing the product to be analyzed once the product has passed through the microfluidic channels and is substantially separated from the microscaled components; and a sensor for detecting the product to be analyzed.

The plurality of microfluidic channels may be assembled in an array, each microfluidic channel having electrodes on internal walls for delivering the dielectrophoretic force to the test sample traversing through the microfluidic channel. The electrodes are located on opposing or adjacent internal walls of the microfluidic channels.

The microfluidic channels preferably comprise a plurality of plates having an electrode configuration, and a plurality of internal channel structures patterned with electrodes, such that each microfluidic channel represents an elongated pathway for the test sample capable of providing a dielectrophoretic force to the test sample as the test sample traverses the microfluidic channel. The plurality of plates and the plurality of internal channel structures are combined to form the array of microfluidic channels.

A collecting electrode is used to attract the product to be analyzed at an inlet of the sensor. The sensor includes a field effect based sensor, nanowire sensor, nanoribbon sensor, or ion sensitive field effect transistor, and is capable of applying a confining dielectrophoretic force, trapping the product to be analyzed.

The pump may be a micro-pump operating in tandem with micro-valves to achieve a fully automated pathogen detection filtration system capable of miniaturization to a chip-scale design.

The apparatus may also include a microfluidic transport module for transporting the product to be analyzed to a location in the vicinity of the sensor.

In a second aspect, the present invention is directed to an apparatus for pathogen detection comprising: a microfluidic assembly including a plurality of microfluidic channels forming an array, each of the microfluidic channels including: electrodes for establishing dielectrophoretic forces on a test sample separating the portions of the test sample into an analyte and a waste product; and adjacent microchannels for receiving the waste product attracted by a dielectrophoretic force, removing the waste product from the analyte; a condenser including an electrode for localizing the analyte for sensing; and a sensor for detecting the analyte.

In a third aspect, the present invention is directed to a method of pathogen detection comprising: providing a test sample including an analyte together with a waste product in a first chamber; providing a reference solution in a second chamber; transporting the test sample through a plurality of microfluidic channels; generating opposing dielectrophoretic forces on the test sample as the test sample is transported through the plurality of microfluidic channels; separating the waste product from the analyte by the opposing dielectrophoretic forces and directing the waste product to a third chamber and the analyte to a condensing area; condensing the analyte in a localized area; flushing the analyte with the reference solution to remove substantially all of remaining waste product from the condensed analyte; detecting low amounts of analyte using a microfluidic sensor.

Dielectrophoretic manipulation of the analyte to the microfluidic sensor is achieved to overcome a diffusion limitation and enable analyte contact with the microfluidic sensor surface for detection.

A pharmaceutical or other substance may be introduced which pierces membranes of an alive analyte component in the reference solution at a predetermined frequency, but not membranes of other analyte components or dead analyte components, and differentiating the alive component from other analyte components and dead analyte components through dielectrophoretic forces.

The method uses the change of a Clausius-Mossotti factor, $CM(\omega)$, upon a change of a medium permittivity, $\in_m$, for analyte capture and release.

The process of capturing the analyte includes: applying an electric field causing a positive dielectrophoretic force to the analyte to facilitate analyte capture; changing the Clausius-Mossotti factor by the flushing; and causing a negative dielectrophoretic force under the electric field acting on the analyte with the changed Clausius-Mossotti factor to facilitate release of the analyte.

The pH or conductivity of the test sample may be adjusted for control of voltage and frequency dependence for the Clausius-Mossotti factor cross-over frequency.

Change of the Clausius-Mossotti factor cross-over frequency may be induced for the analyte by adding or mixing an additional fluid.

The step of separating the waste product from the analyte by the opposing dielectrophoretic forces and directing the waste product to a third chamber and the analyte to a condensing area includes: providing a microfluidic assembly including a plurality of microfluidic channels forming an array, each of the microfluidic channels including: electrodes for establishing dielectrophoretic forces on the test sample separating the portions of the test sample into the analyte and the waste product; and adjacent microchannels for receiving the waste product attracted by a dielectrophoretic force, removing the waste product from the analyte; transporting the analyte to the condenser area; and localizing the analyte at the condenser area by a condenser electrode.

The step of detecting low amounts of analyte using a microfluidic sensor includes using an electric field at predetermined flow conditions, to immobilize the analyte on the surface of a field effect based sensor, nanowire sensor, nanoribbon sensor, or ion sensitive field effect transistor sensor.

Superpositioning or tuning of frequency components, waveform shapes, and waveform tunings, or any combination thereof, may be performed to maximize separation, differentiation, capture, or release of the analyte.

In a fourth aspect, the present invention may be directed to a filtration system for pathogen detection comprising: microchannels for fluid transport; a dielectrophoretic separator for separating the fluid into constituent components; a dielectrophoretic condenser for condensing at least one constituent component of the fluid; a dielectrophoretic transport module; and a field effect based sensor, nanowire sensor, nanoribbon sensor, or ion sensitive field effect transistor, or any combination thereof, for detecting the at least one constituent component of the fluid.

The dielectrophoretic separator includes a parallel multichannel structure having a plurality of microfluidic channels in multiple stacked layers, and branched with waste channels.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 8 depicts a table (Table I) providing values of the coefficient α for RBC, WBC, and bacteria at 10 MHz in blood serum;

FIG. 10 depicts a table (Table II) providing values for the real and imaginary permeability as well as the particle radius and conductivity of *E. Coli* and *Micrococcus* in a reference solution and blood serum;

DESCRIPTION OF THE PREFERRED EMBODIMENT(S)

Figure 1:
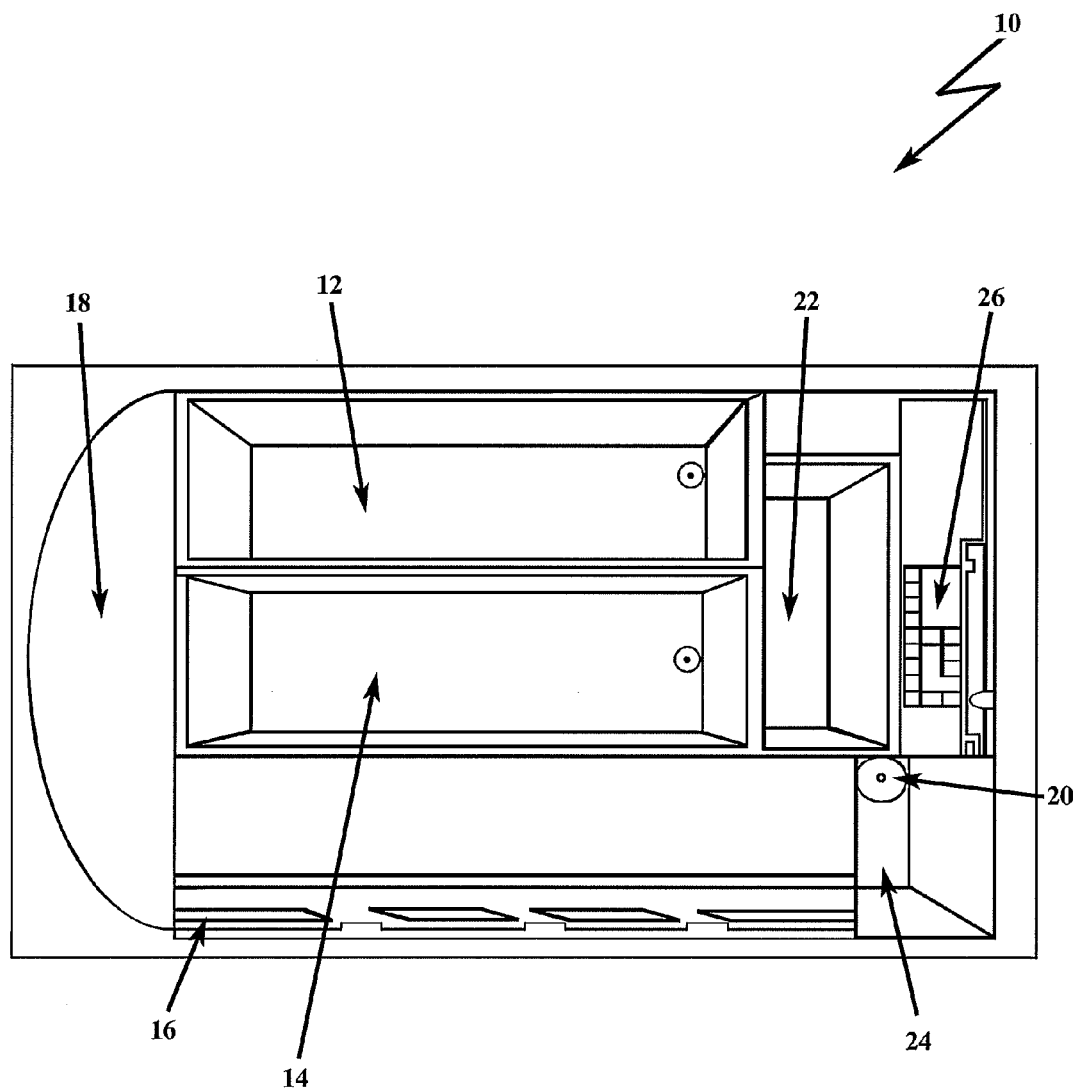
FIG. 1 depicts a filtration system 10 of the present invention for pathogen detection.

In describing the preferred embodiment of the present invention, reference will be made herein to FIGS. 1-17 of the drawings in which like numerals refer to like features of the invention.

The filtration system of the present invention performs pathogen detection using a plurality of dielectrophoretic modules of microfluidic channels with distinctive functionality and geometry to obtain separation performance which cannot be obtained in the prior art. Additionally, the present invention integrates a nano-scaled sensor with the filtration system. Advantageously, all components of the filtration system may be embedded, forming an integrated electronic-microfluidic circuit.

The assembled filtration system automatically transports, separates, condenses, and detects low amounts of particles, cells, and bacteria, or the like, from liquids in a portable configuration that minimizes false positives and negatives.

The present invention defines a robust method for separating bacteria from blood components based on their dielectric properties, localizing the bacteria, flushing substantially all remaining by-products from the bacteria, which generally are on the order of micro-sized or microscaled components, and detecting low concentrations of the bacteria. The separation is fast and reliable as species movement is caused by a module array imparting dielectrophoretic forces, which may be opposing forces for enhancing separation. The module array includes a plurality of microfluidic channels with connecting microfluidic waste channels for directing undesired material away from bacteria. The process enables separation of low concentration of bacteria or other pathogens or particles from blood or other fluids, which then enables detection of the low concentration of these species. This is of great importance for medical diagnostics and determining food safety.

In a preferred embodiment, the invention includes an electronic device capable of detecting of a low number of bacteria or other pathogens or particles from milliliter or larger volumes of different liquid media on a minute time scale by integrating a plurality of modules of microfluidic channels capable of performing a dielectrophoresis-based separation, and incorporating a unique capture system using field-effect-transistor based biosensors.

Bacteria present in a sample even of different types will be subject to a dielectrophoretic force in one direction, whereas all large blood components red blood cells and white blood cells will be subject to a dielectrophoretic force in another direction. Effective separation improves the detection of pathogens. Without separation, blood components which constitute a vast majority of micro-sized particles in blood, would clog active sensor sites and prevent detection of low concentrations of bacteria present in the same sample.

Furthermore, many types of sensors cannot operate in high ionic solutions such as blood plasma. Consequently, the solution containing the sample to be sensed, most likely bacteria, has to be changed to a more suitable reference solution, such as a buffer. Often a pre-concentration step is required. The capture/release mechanism presented by the present invention provides an excellent method for solution exchange without cell loss.

Electric field cell capture, release, and separation based on forces acting in opposite directions allow precise control of cell separation without risk of cell loss or contamination. Advantageously, the present invention may be applied for separating any species of comparable size in any liquid medium; however, bacteria separation from blood components, white blood cells and red blood cells, is illustrated for exemplary purposes, and represents a predominate utilization of the present invention.

FIG. 1 depicts a filtration system 10 of the present invention for pathogen detection. The system includes two injection chambers: a first injection chamber 12 containing a sample to be tested, such as blood, and a second injection chamber 14 containing a reference solution, buffer, or other liquid for flushing at a later point in the process, generally referred to as the by-product or waste-product. Injection chambers 12, 14 are connected to micro-pump inlets which connect to a microfluidic separator 16. Fluids will be pumped into microfluidic separator 16 in a controlled manner by pump 18 such that the test sample (e.g., blood) will be pumped in first. As will be discussed in further detail below, the microfluidic separator includes a plurality of microfluidic channels assembled in an array fashion that uses dielectrophoretic forces to separate continually during transport components of the test sample from one another. In the illustrative example, bacteria may be separated from red and white blood cells. The separated analyte (bacteria) is then condensed by a localized electric field, and reference solution, such as a buffer fluid, is used to replace and dilute or change the chemical composition of the blood serum that reaches condenser 20.

Unlike the prior art, the microfluidic separator 16 of the present invention includes a plurality of channels that apply dielectrophoretic forces that are exerted on the particles, cells, bacteria, and/or micro-scale components as they flow through the channels. The dielectrophoretic field is carefully chosen such that the components of interest that flow through will experience an opposite force as compared to the rest of the components or waste-products that are desired to be separated out. The waste-products are drained throughout the process from the plurality of microfluidic channels to waste chamber 22 through multiple microfluidic channel outlets.

In this manner, the filtration system of the present invention is composed of modules/segments each tuned such that the class of objects under study (i.e., the analyte) has the same response. For example, all bacterial have an nDEP, which is in the middle of the response spectrum. An additional "filter" is then applied for increased accuracy of targeting the analyte. The assembly of independent modules for this application is comprised of multiple, but not necessarily continuous, wires. Microchannel outlets, waste channels, break the continuous wire configuration. Using this geometry, surface electrode configurations may be employed, moving away from continuous conducting wire of the prior art.

In this example, isolated bacteria flows into a condenser chamber 24, which has a collecting electrode to attract the bacteria to the inlet of a microfluidic sensor 26 containing sensor arrays. Movement of bacteria to the field-effect-transistor based sensor is enhanced using the electric field and the dielectrophoretic force to overcome the diffusion limitation of the motion. Furthermore, the present invention is capable of tuning the electric field such that predominantly only the particle of interest is isolated, the remaining product is substantially eliminated. Thus, the analyte may be detected without any labeling or marking process steps, since the analyte is substantially isolated from other related product. This makes the detection essentially label-free, it does not require sensor functionalization with specific antibodies or other known tags for labeling.

The method is based on dielectrophoretic separation followed by dielectrophoretic concentration, and replacement or partial replacement or dilution of the original liquid with at least one reference solution, preferably a conducive solution. The next step is dielectrophoretic manipulation of bacteria to the sensor surface to overcome the diffusion limitation and enable bacteria contact with the sensor surface for detection.

The device operation and automated sample preparation is described in some detail below. First, a test sample injection is distributed into the system. This is performed by a pump that causes the automated distribution of the test sample, placing the test sample in a plurality microfluidic channels (microchannels) via capillary forces (porous media) and pump-pressure driven flow. Each of the plurality of microfluidic channels are lined with electrode geometry capable of establishing an electric field and a dielectrophoretic force on the test sample. Separation within the microfluidic channels is then performed by the dielectrophoretic force. In order to achieve adequate and efficient separation, waveform tuning of the electric field is selected with the intention that two types of species are subjected to forces acting in opposite directions. The separation occurs within microfluidic separator 16. The unwanted micro-scaled components and blood cells (waste-product) separated from the analyte (bacteria/cells/particles) are collected in waste chamber 22. The separated analyte is then collected on condenser 20. An electrode immobilizes the desired analyte material.

In order to remove the waste-product, extraneous serum and other unwanted blood products, the remaining analyte is exposed to a reference solution while held by the condenser electrode. In this manner the unwanted blood products are flushed away, replaced or at least partially replaced, and/or diluted by the reference solution. The remaining analyte is localized to a sensor surface. Dielectrophoretic manipulation of bacteria is used at the sensor surface to overcome the diffusion limitation and enable bacteria contact with the sensor surface for detection.

Preferably the sensor is of nanowire or nanoribben technology, which enables the filtration system of the present invention to be integrated on a semiconductor chipset. Once the final analyte is interrogated, the output may be digitized for automated data processing and readout.

In a preferred embodiment, a multi-step approach to filtration for pathogen detection is achieved using a plurality of dielectrophoretic modules including a plurality of microfluidic channels in an array fashion. The microfluidic separator 16 separates the test sample components of interest (e.g., bacteria) from pollutants (e.g., blood cells and blood serum). In a subsequent process step, the surrounding medium is then exchanged or diluted with a reference solution more suitable for comprehensive electronic detection applications.

The process introduces condensation of the analyte onto a concentrating electrode using a dielectrophoretic (pDEP) force. Once all remaining analyte from the sample is collected on the condensing electrode and the remaining waste-product has been exchanged with the reference solution, the frequency of the applied electric field is then changed (generally from high to low) so that the dielectrophoretic force changes sign and becomes repulsive, and the analyte is then released into a small (~1 μl) volume of the reference solution. Next, the analyte is transported to the sensor chamber and restricted in the vicinity of the sensor. Detection is then performed by sensor arrays, selectively functionalized for the target analyte (bacteria) of interest.

Figure 2:
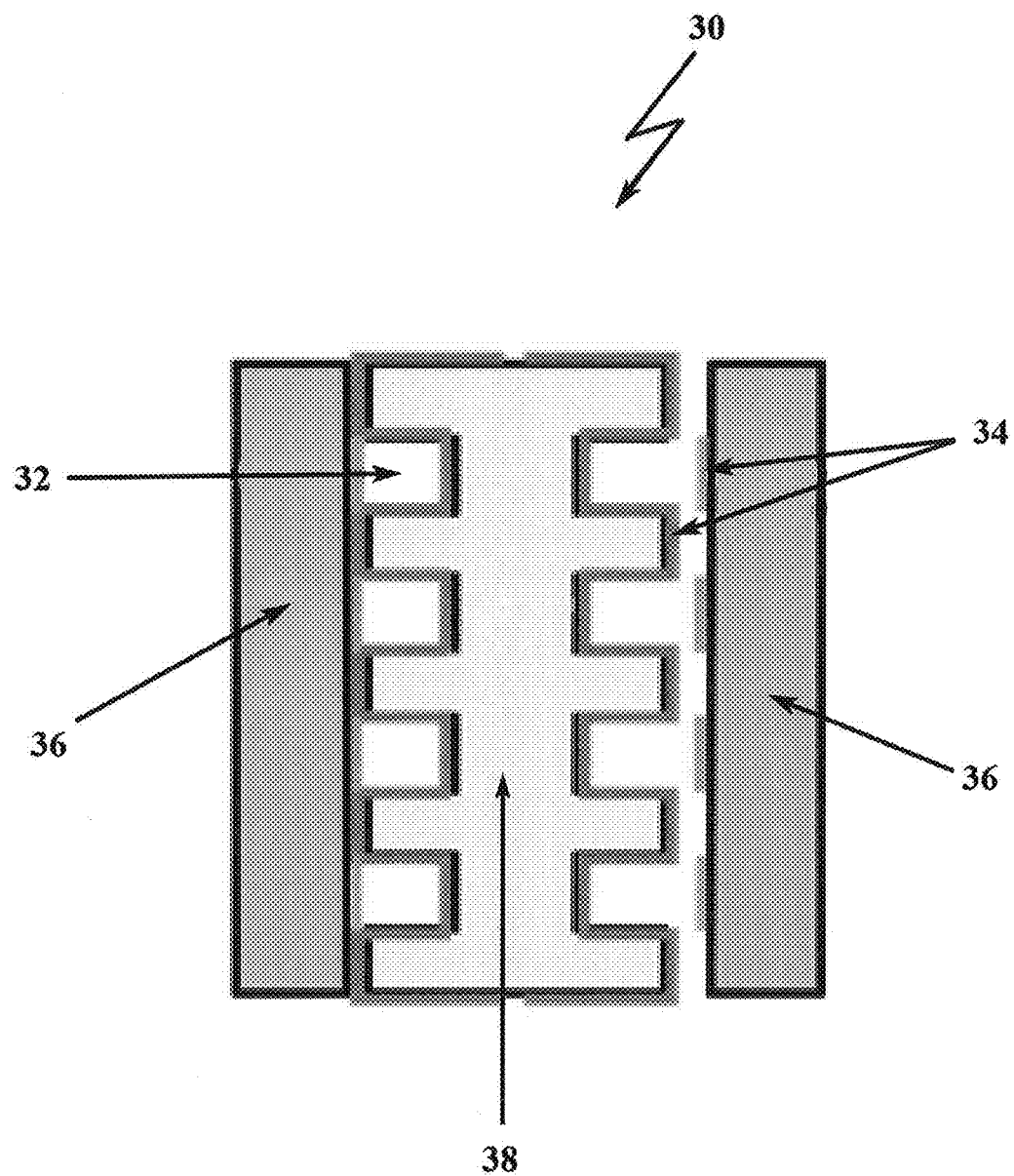
FIG. 2 is a schematic view of a microchannel assembly having a plurality of individual microchannels.

Microfluidic separator 16 is comprised of a high throughput system of multiple microchannels, preferably an array 10×100 microchannels although any number of microchannels may be utilized with varying degrees of efficiency. FIG. 2 is a schematic view of a microchannel assembly 30 having a plurality of individual microchannels 32. Each microchannel assembly 30 has multiple-outlet linear microchannels 32 with copper/metal sets of electrodes 34 deposited on the microchannel walls. In a preferred embodiment, microfluidic microchannel assembly 30 includes plates 36 patterned with metal electrodes 34, such as copper and the like, on each side, generally having a preferred geometry of 5 μm×10 mm×1 μm, sandwiching an internal channel structure or "tree" 38 outlined with copper electrodes 34. When plate 36 comes in contact with internal channel structure 38, multiple microfluidic channels are formed. Plates 36 and internal channel structure 38 may comprise plastic material or other light, durable material capable of securing metal electrodes, and containing the test sample without degradation.

Figure 3:
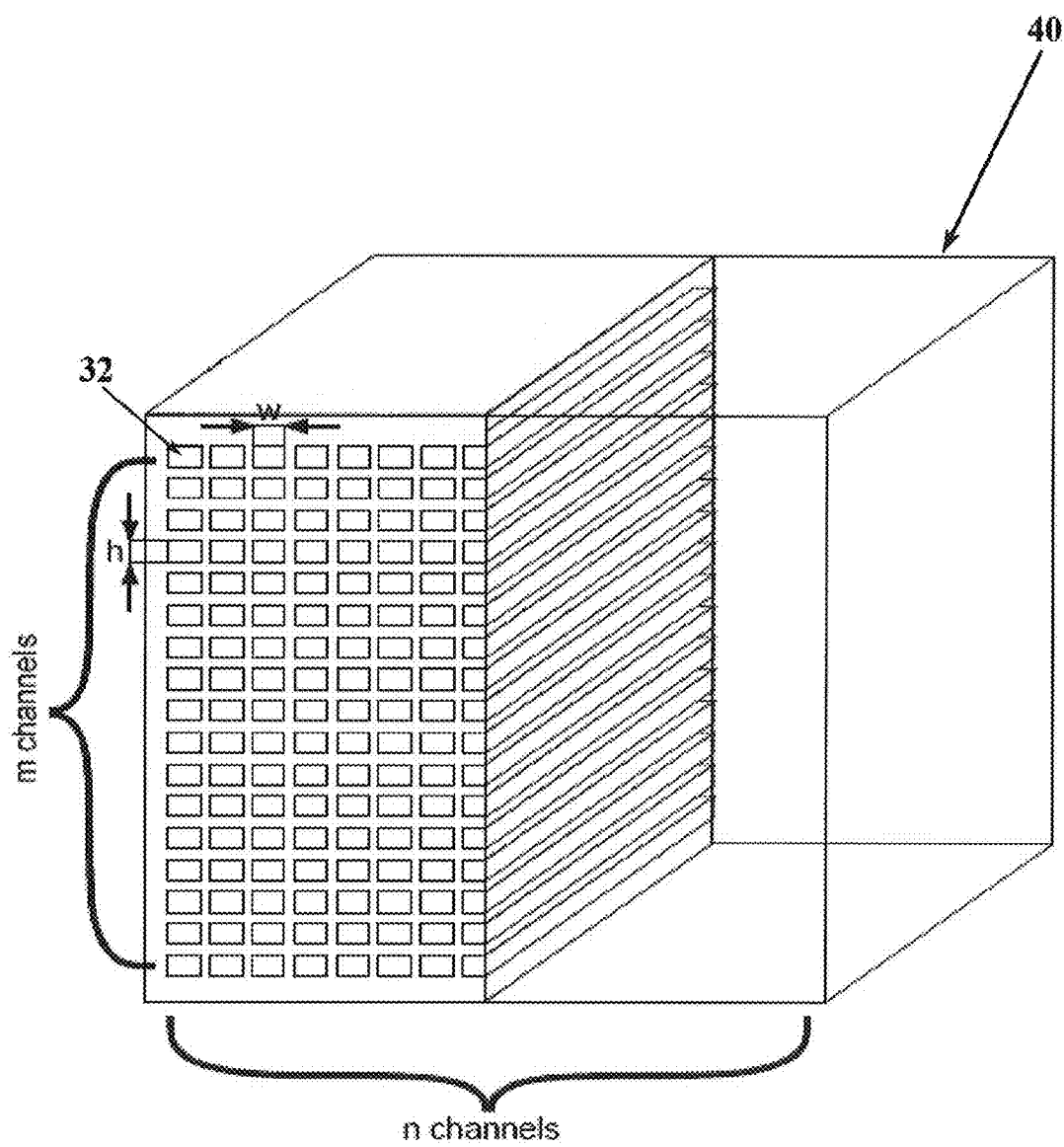
FIG. 3 is a schematic view of an array of microfluidic microchannel assemblies of the present invention used for separation.

FIG. 3 is a schematic view of an array 40 of microfluidic microchannel assemblies 30 of the present invention used for separation. The invention provides for an assembly of layers with defined components of multiple microchannels. Microchannel assemblies 30 are stacked such that array 40 comprises an "m×n" microchannel array. Each microchannel 32 has a height h and width w. In a preferred embodiment, each microchannel 32 is approximately 100 μm wide and 100 μm high. The preferred length of each microchannel 32 is 10 mm. Other dimensions may be pre-determined for particular efficiencies and for specific test samples. The advantage of an array of microfluidic channels is the ability to transport and separate the test sample in an extremely small package—on the order of an integrated circuit. The chip-set size of the filtration system promotes reliability, portability, and discrete packaging.

In a preferred embodiment, array 40 is composed of multiple plates 36 sandwiching internal channel structures 38 such that when stacked they form an array of 10 (horizontal)× 100 (vertical) microfluidic channels. The 11 layers are aligned to the edges and thermally bonded.

In an assembled microfluidic separator 16, laminar flow conditions are provided for separation. Under preferred operating conditions, flow velocity, v, is approximately 100 μm/s, channel length, L, is about 1 cm, the total flow time through a single channel, $t_{flow}$, is on average about 100 s, and the flow rate per channel is about 1 nL/s. Thus, in total 1 cc is pumped very quickly through 1000 microchannels.

The test sample throughput may be "tuned" by increasing or decreasing the number of parallel microchannels, increasing or decreasing the parallel stacked microchannel assemblies 30, and changing the flow velocity by setting the pumping speed.

The invention utilizes the frequency dependence of the sign of the CM factor between different contaminant/blood species for separation in a series of custom designed dielectrophoretic modules.

For the purposes of the present invention, a coefficient α will be defined as follows:

$$\alpha = 2\pi \in_m r^3 \text{Re}\{CM(\omega)\}; \text{ and}$$

$$F_{DEP} = \alpha \cdot \nabla E^2;$$

where CM(ω) is as defined previously. The α coefficient accounts for the particle size r and the dielectric properties of the particle itself $\in_p$ and the surrounding medium $\in_m$.

Thus, the invention provides for separation of species based on the different signs of the Re{CM(ω)} factor and which follows the different signs of the α coefficient at a chosen operating frequency. The separation method of two select groups of the components of interest, i.e., pathogens/cells/bacteria/particles (group 1) and blood cells (group 2), is based on tuning the electric field frequency such that the Re{CM(ω)} factor is positive for one group and negative for the other group. This causes component movements in different directions, which leads to separation. Unlike the prior art, the microfluidic separator is uniquely designed to complete separation, and the subsequent condensing and flushing process steps result in pure isolation of the bacteria, cells, or particles of interest.

A description for bacteria in blood is provided below for the separation, capture, and release mechanisms, and for flow conditions inside a microfluidic channel. Figures of force fields are generated from program runs using COMSOL Multiphysics software.

Figure 4:
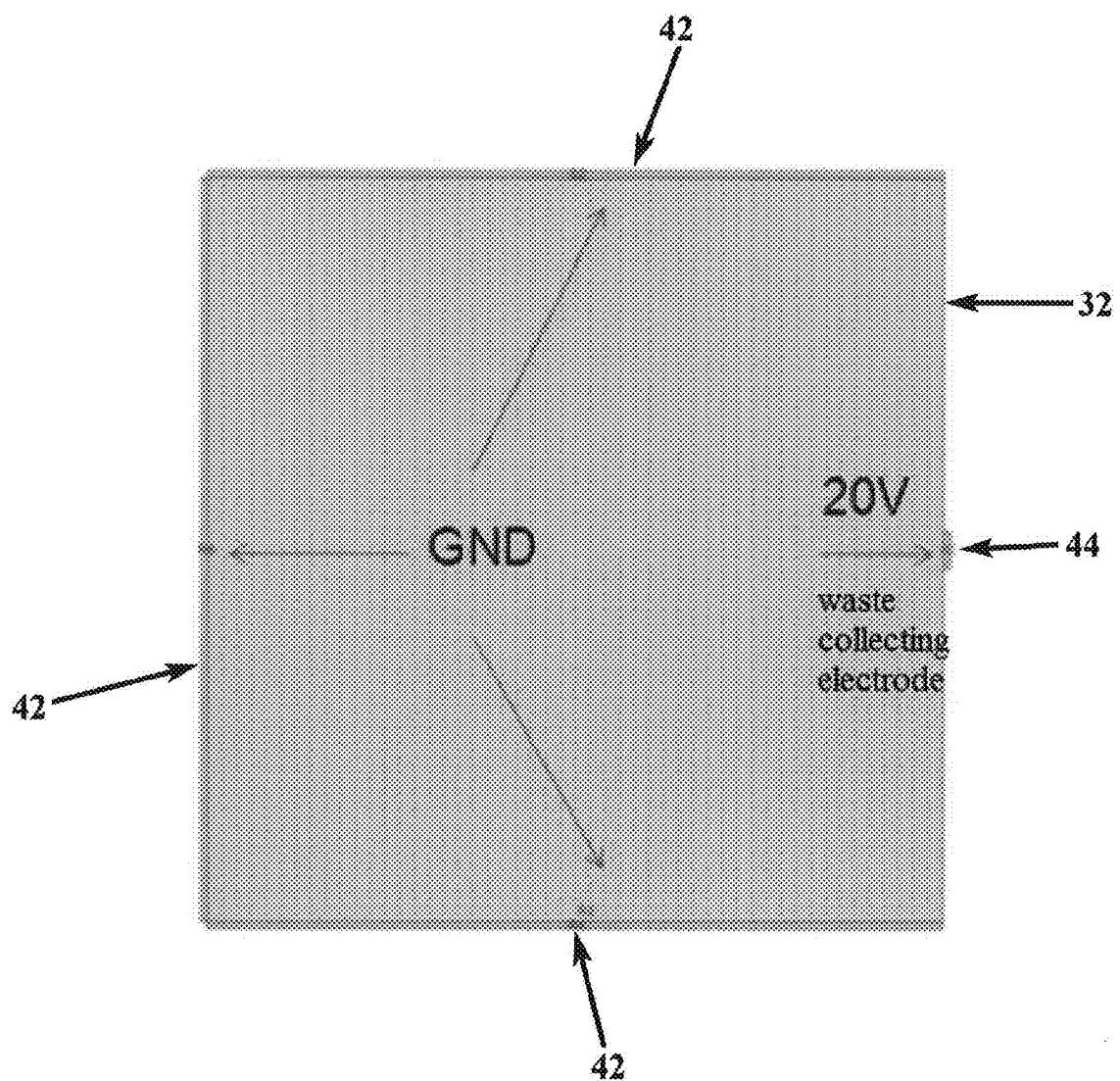
FIG. 4 depicts a cross-section of microchannel with ground electrodes and waste collecting electrode.
Figure 5:
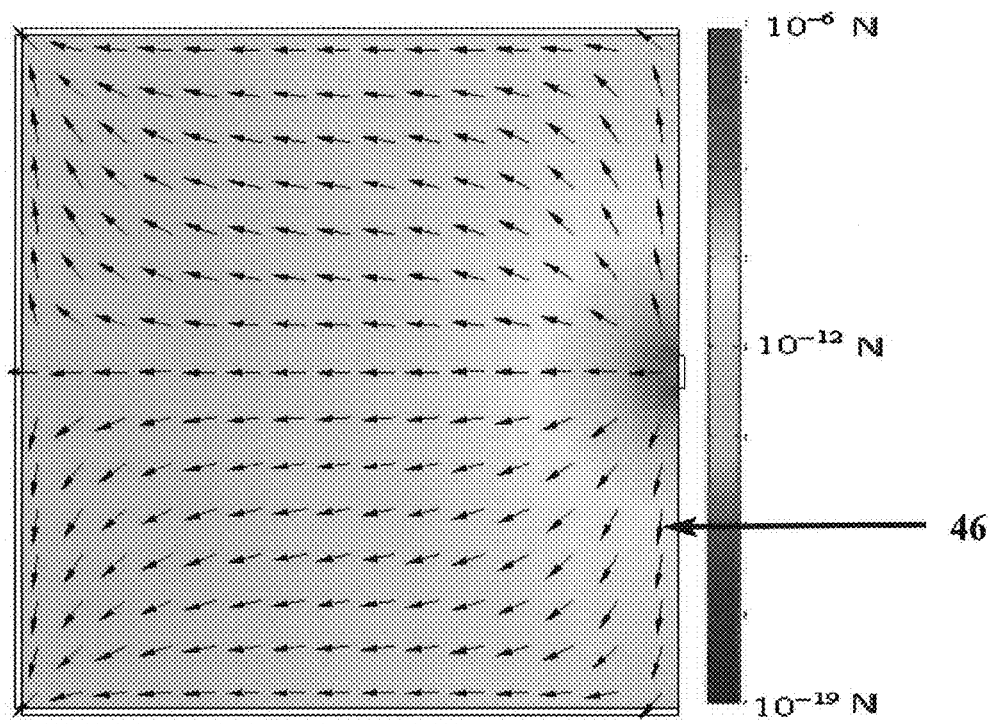
FIG. 5 depicts a computer generated model of the resulting dielectrophoretic forces $F_{DEP}$ acting on bacteria in microfluidic channels.
Figure 6:
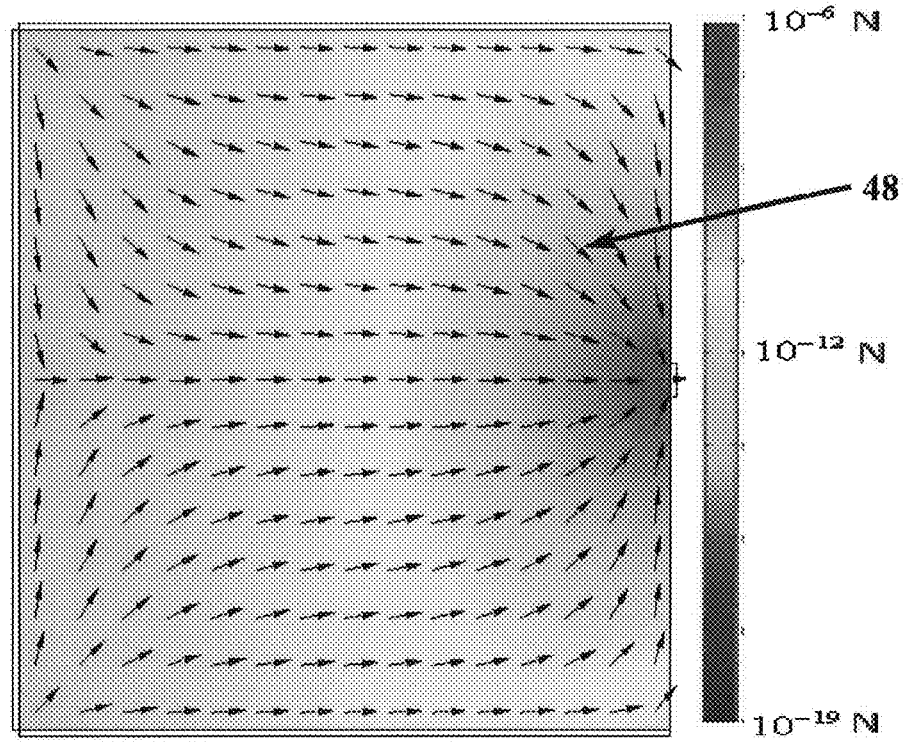
FIG. 6 depicts a computer generated model of the resulting dielectrophoretic forces acting on red blood cells in microfluidic channels.

An electric field gradient is generated by an electrical waveform applied to sets of electrodes on the plurality of microchannel walls. FIG. 4 depicts a cross-section of microchannel 32 with ground electrodes 42 and waste collecting electrode 44. In this example, 20 volts are applied to waste collecting electrode 44. The resulting dielectrophoretic forces $F_{DEP}$ acting on bacteria are depicted by arrows 46 in FIG. 5, while the dielectrophoretic force acting on red blood cells are shown by arrows 48 in FIG. 6. These forces indicate that $F_{DEP}$ for bacteria has an opposite direction from $F_{DEP}$ for red blood cells.

Figure 7:
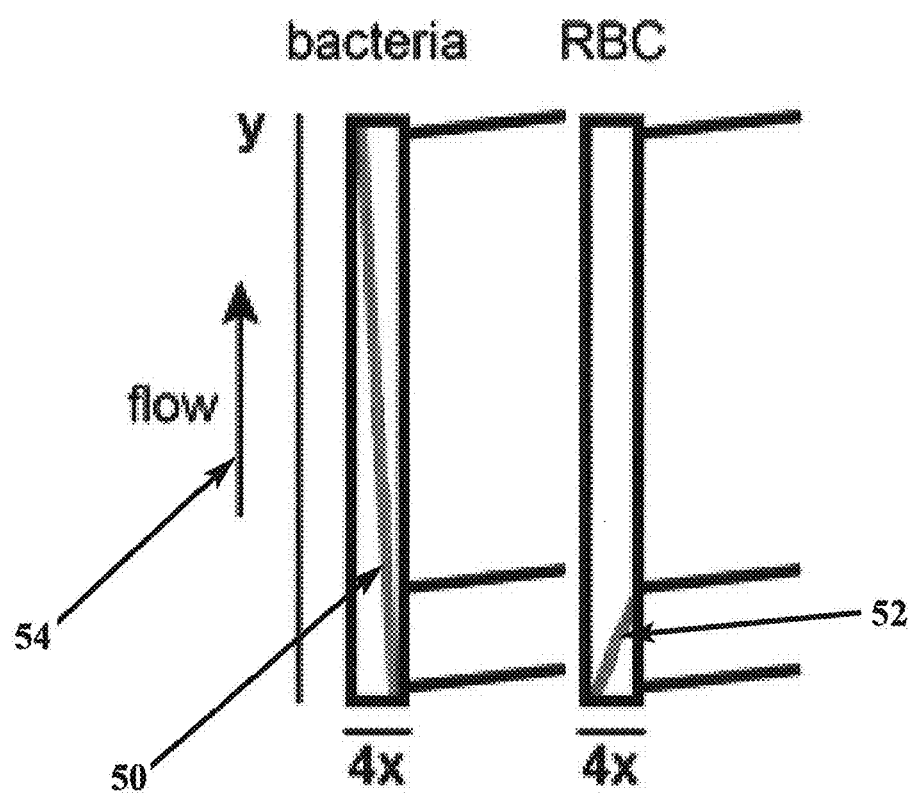
FIG. 7 is a cross-sectional top view of a microchannel showing the trajectories of the test sample components.

FIG. 7 is a cross-sectional top view of a microchannel 32 showing the trajectories of the test sample components. Trajectories of bacteria 50 and red blood cells 52 in the direction of flow 54 are depicted for pre-determined electrode geometry inside one of the many microfluidic channels 32 that comprise microfluidic separator 16. Under the applied wave form, bacteria and red blood cells are pushed towards opposite ends of the microchannels.

As an illustrative example, the values of α are selected for *E. Coli* bacteria, red blood cells, and white blood cells based on pre-determined permittivity data (real and imaginary permittivity $\in_p$, $\in_m$, particle radius r, and conductivity σ).

The dielectrophoretic force acting on *E. Coli* bacteria, red blood cells (RBC), and white blood cells (WBC) is generated by applying a voltage, which in the preferred embodiment is approximately 20V, on the electrodes at different operating frequencies. Selected analytical values for the coefficient α for RBC, WBC, and bacteria at 10 MHz in blood serum are shown in Table I identified in FIG. 8. These values may be altered to effectuate a more defined response electric field, and therefore a selectable dielectrophoretic force.

In Table I (FIG. 8), the real and imaginary part of the complex dielectric function, conductivity, coefficient α, and the real part of the Clausius-Mossotti factor are calculated at 10 MHz for two different types of bacteria (*E. Coli* and *Micrococcus*), white blood cells (T lymphocytes, monocytes, B lymphocytes, and granulocytes), and red blood cells.

Figure 9:
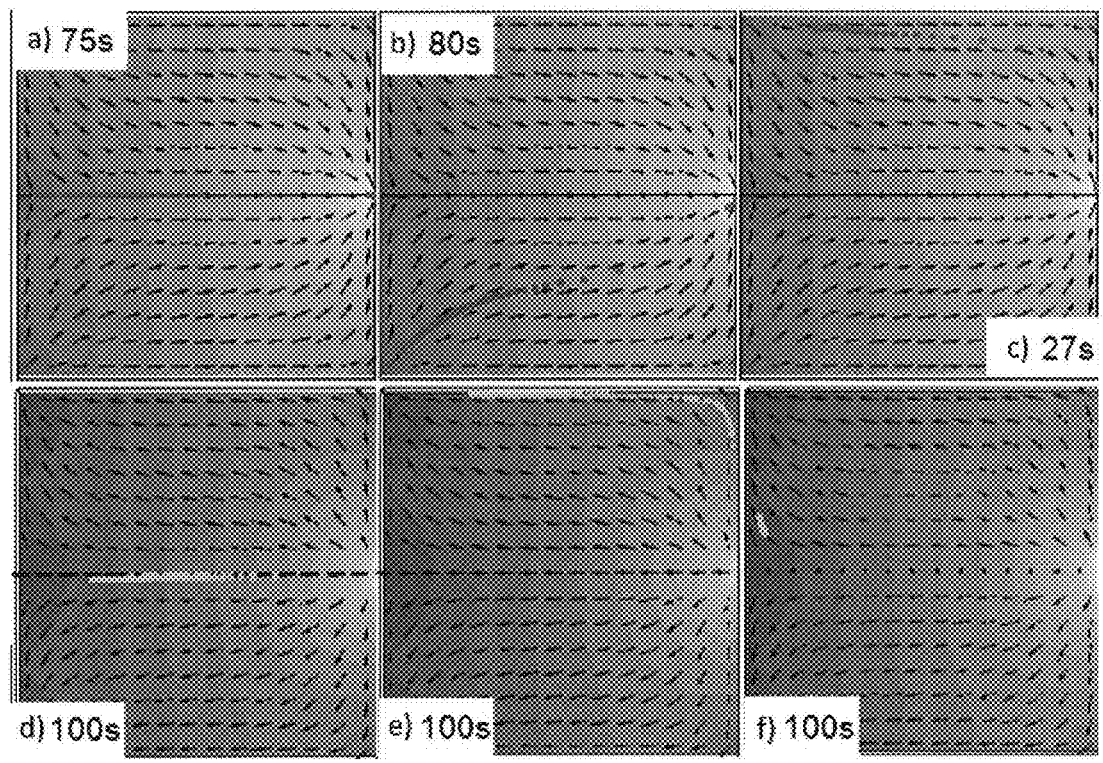
FIG. 9 depicts a computer generated model of bacteria and red blood cell trajectories upon applied dielectrophoretic force in a microfluidic channel.

In this example, α is negative for bacteria and positive for the blood components, thus effecting separation under dielectrophoretic force. At an electric field frequency of 10 MHz, and using blood serum as a surrounding medium, bacteria (*E. Coli* and *Micrococcus*), experience a negative dielectrophoretic force, while at the same operating conditions the blood components, WBC and RBC experience a positive dielectrophoretic force. Bacteria and red blood cell trajectories upon applied dielectrophoretic force in the microchannel are depicted in FIG. 9. Arrows denote the direction of the dielectrophoretic force acting on red blood cells and bacteria. The time based trajectory of motion for different initial positions of red blood cells is depicted in boxes a, b, and c. The time based trajectory of motion for different initial positions of bacteria is depicted in boxes d, e, and f. As shown, red blood cells initially positioned near microchannel walls far from the blood cell collecting electrode reach the blood cell collecting electrode in less than one hundred seconds. In the same electric field, bacteria are pushed away from the blood cell collecting electrode and directed towards the channel medium.

The dielectrophoretic force acting on red blood cells is directed towards the field maximum, where the waste collecting electrode is placed. The dielectrophoretic force confines bacteria within a certain "safe" region of the microchannel as shown in FIG. 9, boxes d, e, f, while it pushes blood cells in the opposite direction, which is towards the waste collecting electrode and the waste channels as shown in FIG. 9, boxes a, b, c. In this manner, separation occurs continuously during test sample transport through the microfluidic channels, with each microchannel doing its part to separate test sample components.

In the current example, utilizing the preferred array geometry for the microfluidic separator array with lateral and vertical DEP electrodes, the provided separation efficiency of *E. Coli* from RBC and WBC components was nearly 95% in about 15 seconds, and 100% for an approximately 100 micron channel length in a timeframe of approximately one minute. The microfluidic separator comprising an array of microfluidic channels, each acting to separate the test sample and direct waste-product towards a waste chamber.

Unique to the present invention, a branched microfluidic design allows for separated components to be discarded as waste, while the target of interest, for example *E. Coli*, is transferred to a condenser, flushed, and then localized for pathogen detection by an electronic sensor. The invention is not dependent upon a single critical dimension fabrication or alignment, and the waveform frequencies may be tuned to change the differential sign of the Re{CM(ω)} factor for different components to be separated. The cross-over frequency varies for different particles, bacteria, and/or cells in different media.

The values of the α coefficient for bacteria *E. Coli* and *Micrococcus* in buffer solution and blood serum at frequencies 10 MHz and 400 Mhz are provided in Table I of FIG. 8 and Table II of FIG. 10. In Table II (FIG. 10), the pre-determined values for the real and imaginary permeability as well as the particle radius and conductivity are listed. To enhance separation efficiency a pre-determined waveform containing frequency components tuned for particular species (particles/bacteria/cells) of interest is used.

Continuing with the example above, the α coefficient for *E. Coli* and *Micrococcus* is negative and has a different magnitude in blood serum at 10 MHz, which for *E. Coli* α=−0.0044 $(10^{-24})$ $J(m/V)^2$, and for *Micrococcus* α=−0.0027$(10^{-24})$ $J(m/V)^2$, while the α coefficient is positive and has a similar magnitude in blood serum at 400 MHz (*E. Coli* α=0.0044 $(10^{-24})$ $J(m/V)^2$, *Micrococcus* α=0.0043$(10^{-24})$ $J(m/V)^2$). *Micrococcus* and *E. Coli* will experience a very similar force in blood serum at 400 MHz, while they will experience a very different (opposite) force in the same medium, blood serum, at a frequency of 10 MHz.

The α coefficient for T. Lymphocytes is positive (α=0.0136 $(10^{-24})$ $J(m/V)^2$) in blood serum at 10 MHz. Thus, the DEP force (negative DEP) exerted on bacteria in blood serum at 10 MHz has an opposite sign then the DEP force (positive DEP) exerted on T. Lymphocytes in blood serum at 10 MHz.

Consequently, a waveform applied to the electronic device of the present invention, containing only a frequency component at 400 MHz will result in a very similar behavior of both *E. Coli* and *Micrococcus*, causing similar motion of both products. A waveform applied to the electronic device containing only a frequency component at 10 MHz will result in a similar motion of both *E. Coli* and *Micrococcus*, and this motion will be in the opposite direction of T. Lymphocytes.

A waveform applied to the device containing both frequency components 10 MHz and 400 MHz will result in a motion of *Micrococcus* while the force will cancel for *E. Coli*, resulting in a lack of motion of *E. Coli*.

A choice of a waveform in the same medium allows differentiating and fingerprinting different species. Unique to the present invention, a sequence of an array of modules with tuned waveforms would allow selecting species based on their unique dielectric function.

After passing through the segments of microfluidic separator 16, the first component of the filtration system, the targets of interest (e.g., bacteria) are separated from pollutants (e.g., blood cells), at which point, the targets of interest are then condensed by condenser 20.

In a preferred embodiment, condenser 20 uses the change of the Re{CM(ω)} factor upon the change of the medium permittivity ($\in_m$) for species capture on a capturing electrode, to reduce the volume of the sample and condense the species bacteria, cells, and/or particles in a significantly lower volume. A collecting electrode attracts the bacteria to the inlet of a microfluidic sensor 26 containing sensor arrays. Movement of bacteria to a field-effect-transistor based sensor is enhanced using the electric field and the dielectrophoretic force to overcome the diffusion limitation of the motion.

Figure 11A:
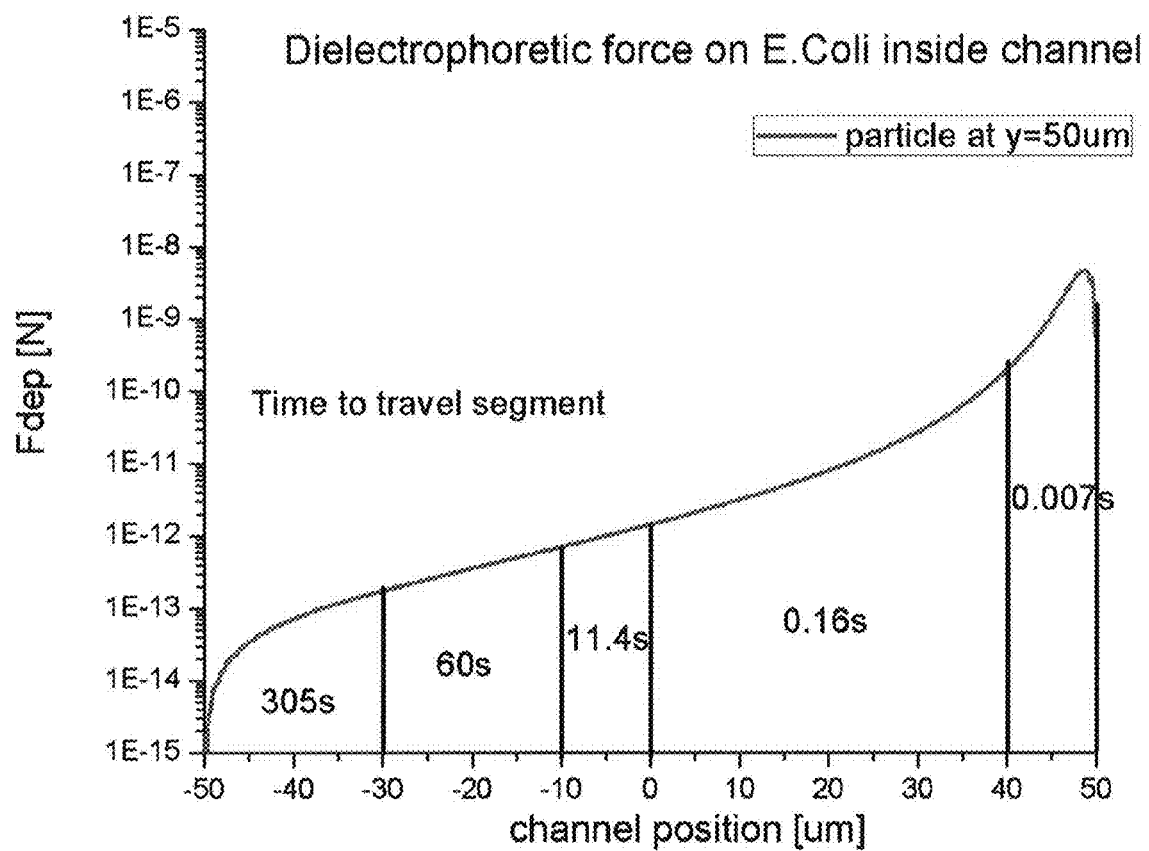
FIG. 11A depicts a graph of a simulation of the dielectrophoretic force on *E. Coli* inside a microfluidic channel as a function of channel position and travel time.
Figure 11B:
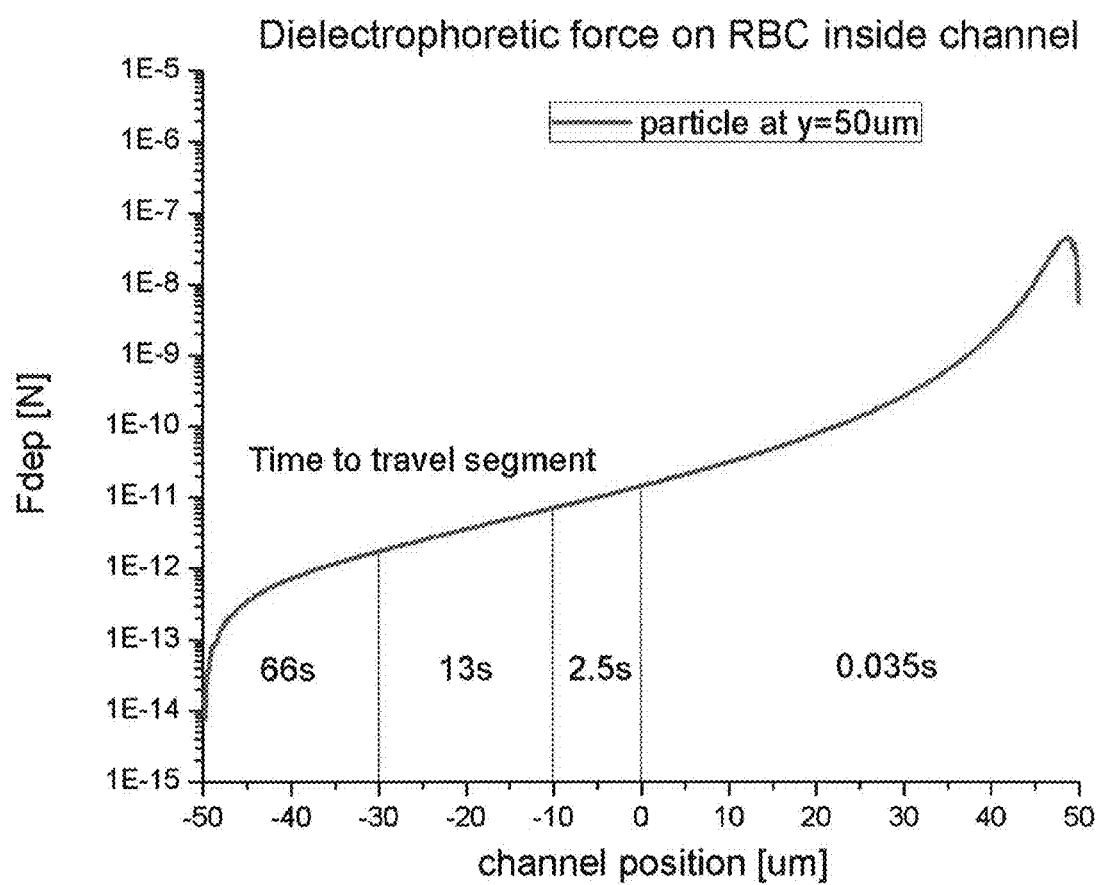
FIG. 11B depicts a graph of a simulation of the dielectrophoretic force on RBCs inside a microfluidic channel as a function of channel position and travel time.

FIG. 11A depicts a graph of a simulation of the dielectrophoretic force on *E. Coli* inside a microfluidic channel as a function of channel position and travel time. FIG. 11B depicts a graph of a simulation of the dielectrophoretic force on RBCs inside a microfluidic channel as a function of channel position and travel time. These simulation results show that bacteria, if placed within 10 μm of the elimination electrode, are repelled towards the safe zone within 0.007 seconds. For RBCs, the elimination time is shorter than 82 seconds. Fifty percent (50%) of the RBCs are filtered out within the first 0.5 seconds. Ninety-five percent (95%) of the RBCs are filtered out within the first 16 seconds, and substantially all of the RBCs are filtered out within the first 82 seconds.

Figure 12:
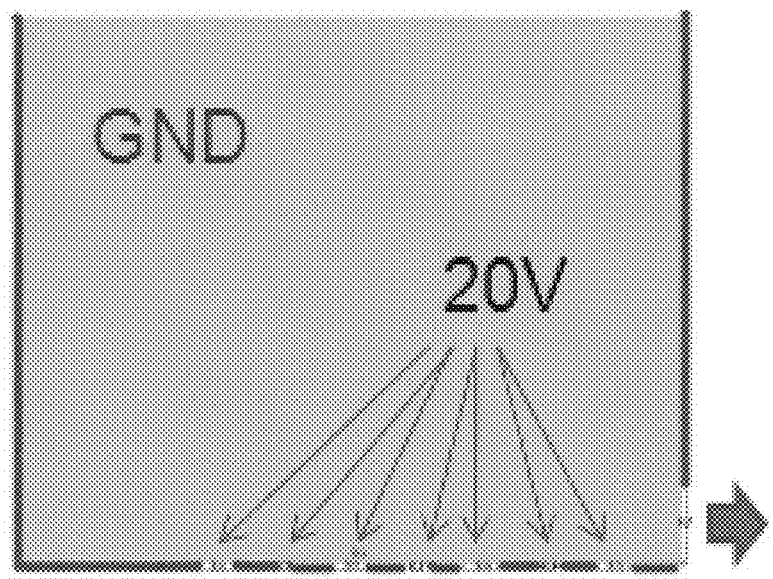
FIG. 12 depicts a set of electrodes and their respective geometry in a cross-section of a microfluidic channel for capturing and immobilizing bacteria.
Figure 13:
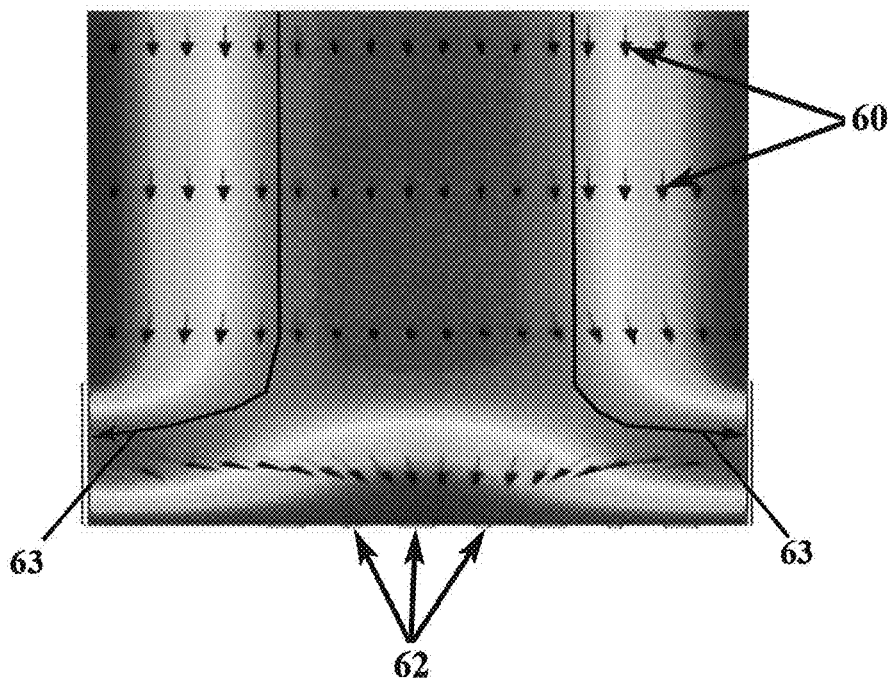
FIG. 13 depicts a force diagram of the resultant electrodes of FIG. 12 showing the direction of the dielectrophoretic force acting on bacteria.

At a matching frequency, the $\text{Re}\{CM(\omega)\}$ in the medium surrounding the species is positive, which results in a positive dielectrophoretic force directed towards a capturing electrode. The set of electrodes and their geometry in the microchannel cross-section is shown in FIG. 12 for capturing and immobilizing bacteria. The direction of the dielectrophoretic force acting on bacteria is shown in the force diagram of FIG. 13. Arrows 60 show the direction of the dielectrophoretic force on bacteria, causing the product to be analyzed, i.e., bacteria, to collect on the electrodes. Despite the flow directed towards the microchannel outlet, bacteria are collected on the collecting electrodes 62 due to a positive dielectrophoretic force and a positive $\text{Re}\{CM(\omega)\}$ factor. Microchannel outlets 63 remove waste and excess fluid being separated from the analyte.

Figure 14:
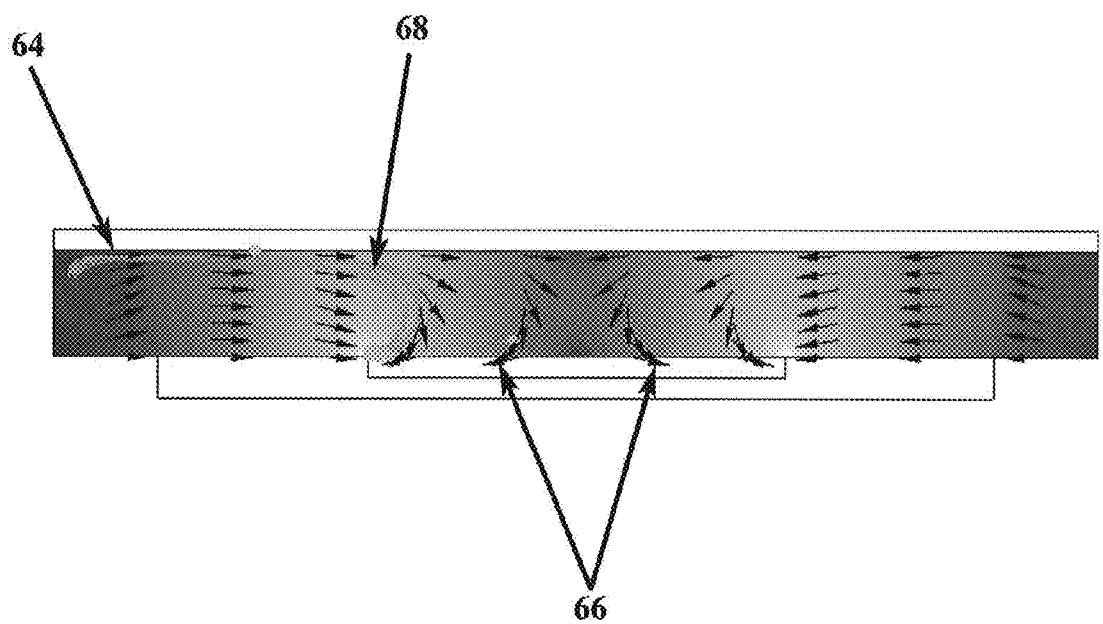
FIG. 14 depicts a flow velocity profile with inflow from left and the dielectrophoresis force directing/pushing bacteria to the sensor at the bottom of a microfluidic channel.

FIG. 14 depicts a flow velocity profile 64 with inflow from left and the dielectrophoresis force directing/pushing bacteria to the sensor at the bottom of a microfluidic channel (overcoming diffusion limitations). Arrows show direction of the dielectrophoretic force acting on bacteria 68. Despite the flow directed towards the microchannel outlet, bacteria are collected on the collecting electrode due to a positive dielectrophoretic force and a positive $\text{Re}\{CM(\omega)\}$ factor. When the surrounding medium is changed by the buffer solution, the value of the $\text{Re}\{CM(\omega)\}$ factor becomes negative, and the dielectrophoretic force repels bacteria from the electrode causing species release.

To enhance separation, overcome the limitation caused by high ionic strength of the solution, and obtain functional analyte (bacteria) response, the initial medium (e.g., blood serum) is diluted and partially replaced by the buffer solution. As a result, the dielectric constant of the medium $\in_m$ changes and the $\text{Re}\{CM(\omega)\}$ factor changes resulting in a change of the magnitude and potentially direction of the force.

The change of the $\text{Re}\{CM(\omega)\}$ factor upon the change of the particle/cell/bacteria permittivity ($\in_p$) is used to obtain a differential functional response.

This form of α-screen testing allows for a portable platform for rapid multiplexed analyte detection, such as bacteria, from blood samples of ill patients at a point-of-care application. Doctors would be able to diagnose the bacteria of infection, and accurately prescribe only the necessary antibiotic, resulting in a more efficient disease treatment, and limiting antibiotic-resistance formation.

Using the apparatus of the present invention, this α-screen testing does not require additional laboratory space, and is low in energy consumption. It may be used with a sensor network integrated with food processing lines in food processing plants for continuous food product quality monitoring, or used in food storage and transport. It may be integrated in a hand-held unit for rapid *Vibrio cholera* and *E. Coli* bacteria detection from water samples to determine water safety.

By introducing to the medium a reference solution, such as a buffer, and additional pharmaceuticals, the dielectric constant of the medium $\in_m$ changes, the dielectric constants of the particles/bacteria/cells $\in_p$ change, and $\text{Re}\{CM(\omega)\}$ change for different species, resulting in a change in $F_{DEP}$ allowing to distinguish between the analyte components.

Using the previous values as an illustrative example, the α coefficient for *E. Coli* and *Micrococcus* is negative and has a different magnitude in blood serum at 10 MHz (*E. Coli* α=−0.0044 $(10^{-24})$ J(m/V)$^2$, *Micrococcus* α=−0.0027 $(10^{-24})$ J(m/V)$^2$), while α is positive in a PBS buffer solution at 10 MHz (*E. Coli* α=0.0055 $(10^{-24})$ J(m/V)$^2$, *Micrococcus* α=0.0106 $(10^{-24})$ J(m/V)$^2$}. The force $F_{DEP}$ on *Micrococcus* in serum will have a lower magnitude than on *E. Coli*; however, in a buffer solution (such as PBS) the force on *Micrococcus* will be stronger than on *E. Coli*. Introducing a pharmaceutical or a substance (antibiotic) which pierces only the membrane of alive *Micrococcus* at 10 MHz in PBS, but not the membrane of *E. Coli* or dead *Micrococcus* in buffer will allow differentiating alive from dead *Micrococcus* and *E. Coli*, since the dielectrophoretic force depends on the size of the particle/bacteria/cell, where $F_{DEP}$ is proportional to $r^3$.

Thus, a tuned chemical modification of the medium allows differentiating and fingerprinting different species. A sequence of modules with tuned chemical modifications will allow species selection.

In the preferred embodiment, the invention applies an electrical waveform and a dielectrophoretic force for enclosing the separated bacteria in a small volume around a sensor to significantly decrease diffusion time to the sensor. Bacteria trapping on a nanowire or nanoribbon sensor is a resultant of the dielectrophoretic trapping mechanism and surface modification of the sensor for capture. In this manner, a dielectrophoretic force is used as a confining force for trapping micro-sized blood components (RBC, WBC, bacteria, and the like).

The DEP capture mechanism for bacteria decreases the volume of diffusion of a product of interest (particle, bacteria, and/or cell) in the sensor chamber, and decreases the time for the product of interest to diffuse towards the sensor surface, which is necessary for detection.

The electronic device that implements this separation may be miniaturized to an integrated circuit, and does not require trained personnel—the user only introduces a sample (such as blood or water) into the inlet chamber, and an automated process performs sampling, separation, condensation, transport, and detection. Using dielectrophoresis, the device automatically separates any present bacteria from the rest of the sample—for example, with blood, the large blood components (e.g., red and white blood cells). The separated bacteria are concentrated by a second dielectrophoretic region, and finally detected using label-free nanosensors which may be functionalized with bacteria specific antibodies for selectivity.

Figure 15A:
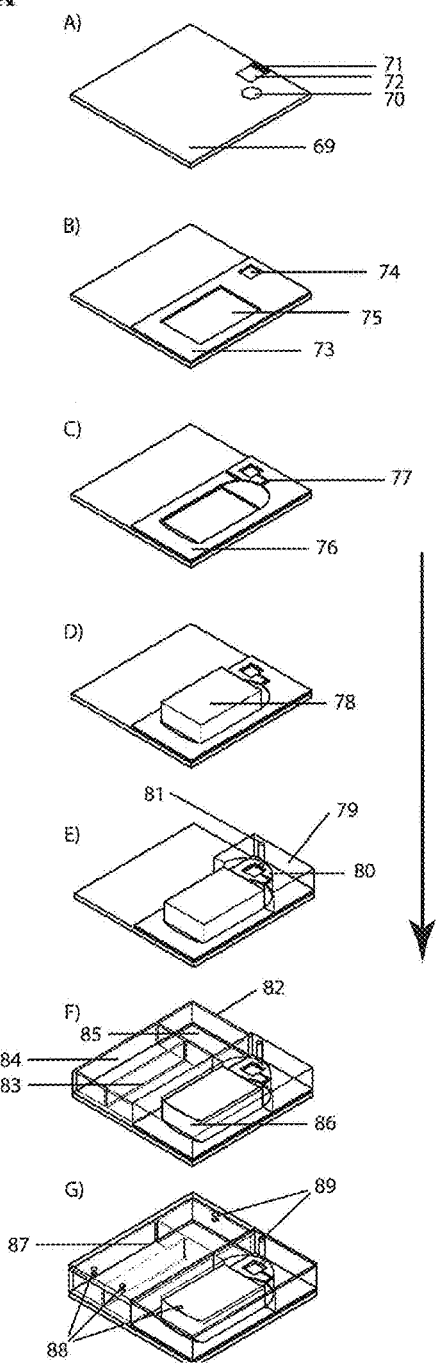
FIG. 15A depicts fabrication levels or steps of integration of the present invention on an integrated circuit chip.

The levels of integration of the present invention on an integrated circuit chip are generally depicted by the fabrication steps of FIG. 15A. Fig. Step A depicts a printed circuit board with an integrated circuit 69, embedded electrode connections 70, 71 and an embedded sensor 72. The subsequent layers and components depicted in Steps B-G are stacked consecutively and thermally and/or chemically bonded to form the device.

Step B of FIG. 15A provides a structure provided in an insulator layer 73 bonded on top (or bottom) of the PCB. The opening 74 is for the sensor chamber, providing access to the sensor and embedding electric connections. The opening 75 is for alignment of the microfluidic separator.

Step C adds insulator layer 76 with openings for the separator, the condenser chamber, and a microfluidic channel connecting chambers, e.g. the condenser with the sensor chamber 77.

Step D depicts the addition of the microfluidic separator module 78.

Step E adds an insulator layer forming the walls of the condenser 79, an electrode 80, and outlet 81 from the sensor chamber.

Step F adds insulator layer 82 forming the walls of the test sample chamber 83, buffer/reference liquid chamber 84, waste chamber 85, and the insulator layer 86 forming the walls of the separator.

Step G adds lid 87 with inlets to the chambers for sample, liquid storing, inlets 88 to the separator, and outlet 89 from the sensor chamber and waste chamber.

Figure 15B:
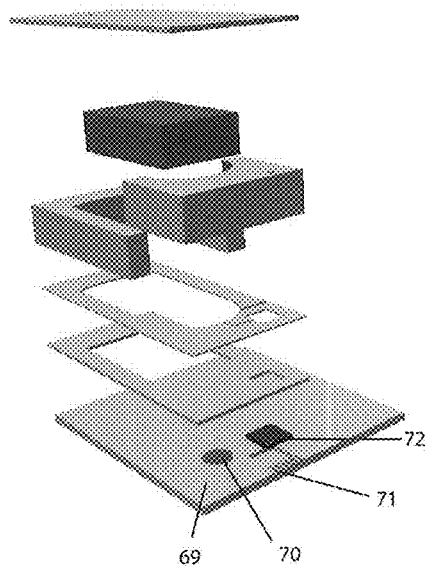
FIG. 15B depicts an expanded assembly drawing of the layers representing the fabrication steps of FIG. 15A.

FIG. 15B depicts an expanded assembly drawing of the layers representing the fabrication steps of FIG. 15A.

Figure 16:
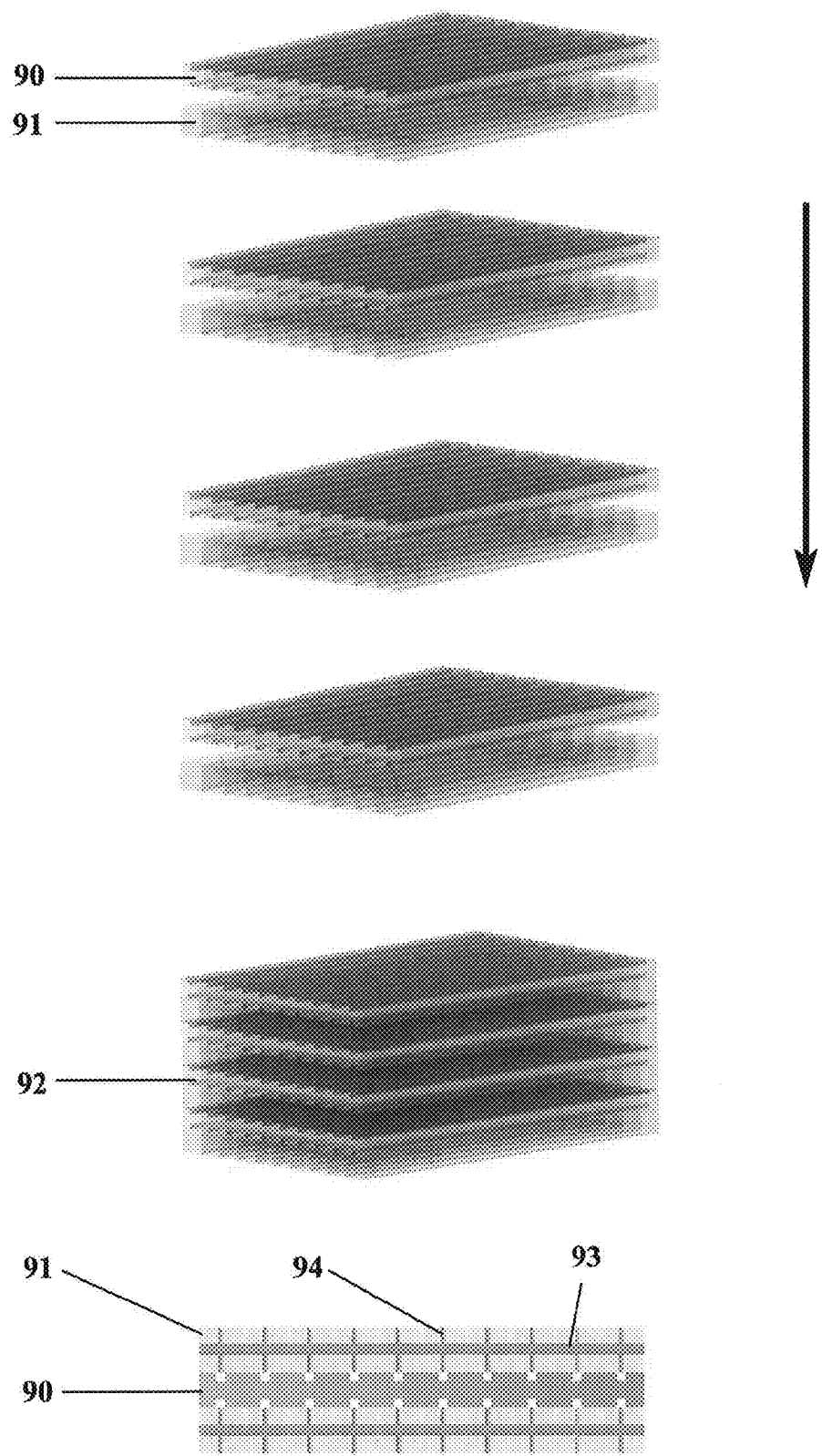
FIG. 16 is an expanded assembly drawing of the layers of a microfluidic separator.

FIG. 16 is an expanded assembly drawing of the layers of a microfluidic separator. The layers include a first layer 90 having microchannel structures and coated with a planar electrode, followed by a second layer 91 having discrete waste electrodes. These layers are stacked in pairs to form a microfluidic separator module 92. The interconnected waste collecting microchannels 93, 94 are located inside of the insulating layers. The described assembly provides customizing the number of microchannels on each layer, the number of stacked layers, and the device throughput.

Figure 17:
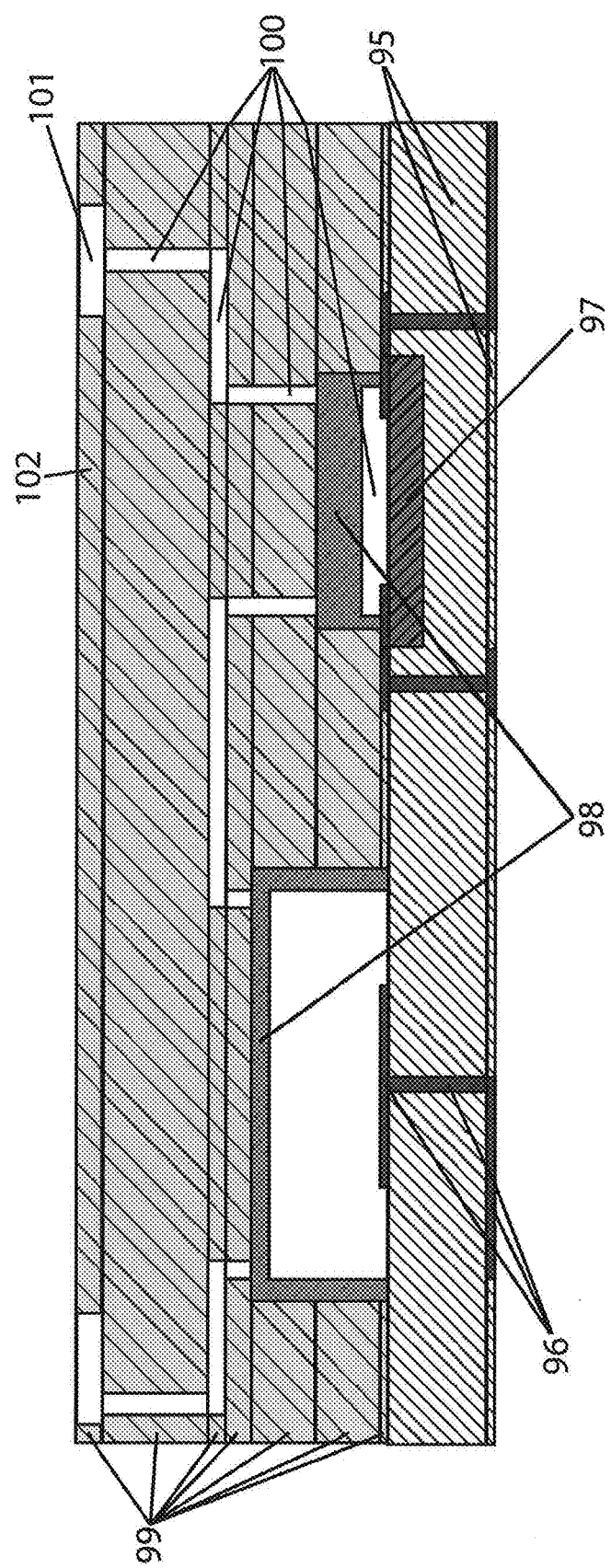
FIG. 17 depicts electrical connections and microfluidic connections between components provided in embedded layers of an integrated circuit device of the present invention.

In one embodiment the electrical connections and microfluidic connections between components are provided in embedded layers as shown in FIG. 17.

FIG. 17 shows a printed circuit board 95 with embedded copper connections 96. An integrated circuit sensor 97 is connected by wire-bonding, BGA, or flip-chip technology to the PCB. A microfluidic channel or chamber 98 is embedded in layers of insulator 99 with openings cut to fit the microfluidic structures 98. The layers of insulator 99 are stacked and thermally or chemically bonded. The openings and holes 100 in the layers of the insulator 99 align vertically and form microchannels for fluid transport. The inlets and outlets 101 to the integrated electronic microfluidic circuit are defined in the top insulator layer 102.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An apparatus for analyte detection comprising:
   a first chamber configured to store a test sample including analyte and microscaled components;
   a second chamber configured to store a reference solution;
   a pump and a plurality of injection chambers configured to introduce said reference solution and said test sample to a microfluidic separator;
   said microfluidic separator including a plurality of plates patterned with metal electrodes on at least one side and a plurality of internal channel structures having electrodes patterned on at least one internal surface wherein each of said plurality of internal channel structures is sandwiched between two of said plurality of plates which together form an array of microfluidic channels, said plate electrodes and said internal channel electrodes configured to provide opposing dielectrophoretic forces on said test sample which separates said test sample into said analyte and said microsealed components;
   a plurality of receiving microchannels adjacent said plurality of microfluidic channels configured to receive and remove said microscaled components;
   a third chamber configured to store said microscaled components when separated from said analyte;
   a condenser configured to capture said analyte once said analyte has passed through said microfluidic separator; and
   a sensor configured to detect said analyte.

2. The apparatus of claim 1 wherein said electrodes are located on opposing or adjacent internal walls of said microfluidic channels.

3. The apparatus of claim 1 including a collecting electrode to attract said product to be analyzed at an inlet of said sensor.

4. The apparatus of claim 1 wherein said sensor includes a nanowire sensor, nanoribbon sensor, or ion sensitive field effect transistor, and is capable of applying a confining dielectrphoretic force trapping said product to be analyzed.

5. The apparatus of claim 3 wherein said sensor includes an array of field effect transistor biosensors.

6. The apparatus of claim 4 wherein said sensor surface includes geometry to enhance capture of said product to be analyzed.

7. The apparatus of claim 1 wherein said pump comprises a micro-pump operating in tandem with micro-valves to achieve a fully automated pathogen detection filtration system capable of miniaturization to a chip-scale design.

8. The apparatus of claim 1 including a microfluidic transport module for transporting said product to be analyzed to a location in the vicinity of a sensor.

9. The apparatus of claim 1, wherein said opposing dielectrophoretic forces tune the electric field such that said analyte is isolated, and any remaining microsealed components are substantially eliminated.

10. An apparatus for analyte detection comprising:
    a microfluidic assembly including a plurality of plates patterned with metal electrodes on at least one side, and a plurality of internal channel structures having electrodes patterned on at least one internal surface,
    wherein each of said plurality of internal channel structures is sandwiched between two of said plurality of plates which together form an array of microfluidic channels, said plate electrodes and said internal channel electrodes configured to provide opposing dielectrophoretic forces on a test sample, which separates said test sample into an analyte and a waste product; and
    a plurality of receiving microchannels adjacent said plurality of microfluidic channels configured to receive and remove said waste product;
    a condenser area including an electrode configured to localize said analyte for sensing; and
    a sensor for detecting said analyte.

11. The apparatus of claim 10 wherein said opposing dielectrophoretic forces allow said analyte to be detected without any labeling or marking process steps.

* * * * *